United States Patent
Kaneko et al.

(10) Patent No.: US 11,697,031 B2
(45) Date of Patent: Jul. 11, 2023

(54) RADIATION THERAPY SYSTEM AND METHOD OF OPERATING RADIATION THERAPY APPARATUS

(71) Applicant: Hitachi, Ltd., Tokyo (JP)

(72) Inventors: Shuji Kaneko, Tokyo (JP); Kunio Takahashi, Tokyo (JP)

(73) Assignee: HITACHI, LTD., Tokyo (JP)

(*) Notice: Subject to any disclaimer, the term of this patent is extended or adjusted under 35 U.S.C. 154(b) by 58 days.

(21) Appl. No.: 17/195,685

(22) Filed: Mar. 9, 2021

(65) Prior Publication Data

US 2021/0299473 A1    Sep. 30, 2021

(30) Foreign Application Priority Data

Mar. 31, 2020    (JP) .................................. 2020-064381

(51) Int. Cl.
*A61N 5/10*    (2006.01)

(52) U.S. Cl.
CPC .......... *A61N 5/1048* (2013.01); *A61N 5/103* (2013.01); *A61N 5/1045* (2013.01); *A61N 5/1081* (2013.01)

(58) Field of Classification Search
CPC .... A61N 5/1048; A61N 5/103; A61N 5/1045; A61N 5/1081; A61N 5/1082; A61N 5/1042; A61N 5/1047
See application file for complete search history.

(56) References Cited

U.S. PATENT DOCUMENTS

| | | |
|---|---|---|
| 2008/0170663 A1 | 7/2008 | Urano et al. |
| 2010/0065749 A1* | 3/2010 | Nomura ............... A61N 5/1048 250/389 |
| 2011/0150186 A1* | 6/2011 | Ziegler ................ A61N 5/1081 378/196 |
| 2011/0210261 A1 | 9/2011 | Maurer |
| 2016/0166858 A1* | 6/2016 | Takahashi ............ A61N 5/1082 600/1 |
| 2018/0008842 A1* | 1/2018 | Kaneko ................ A61N 5/1081 |

FOREIGN PATENT DOCUMENTS

| | | |
|---|---|---|
| JP | 2008-173182 A | 7/2008 |
| JP | 2015-100455 A | 6/2015 |
| JP | 2016-174674 A | 10/2016 |

OTHER PUBLICATIONS

Extended European Search Report received in corresponding European Application No. 21161916.8 dated Aug. 27, 2021.

* cited by examiner

*Primary Examiner* — Marcus H Taningco
(74) *Attorney, Agent, or Firm* — Mattingly & Malur, PC

(57) ABSTRACT

A radiation therapy system is capable of widening a radiation irradiation range to a patient and includes: a radiation source; a rotation mechanism that supports the radiation source in rotation around an isocenter; a couch that places a therapy target site of a patient at the isocenter; a head swing mechanism that is disposed between the radiation source and the rotation mechanism and that swings an irradiation axis of a radiation emitted from the radiation source by swinging the radiation source; and a controller. The controller holds the head swing mechanism in a state where the irradiation axis of the radiation of the radiation source is shifted from the isocenter in a predetermined direction by a predetermined amount, and rotates the radiation source by the rotation mechanism while emitting the radiation from the radiation source while maintaining the state of the head swing mechanism.

6 Claims, 16 Drawing Sheets

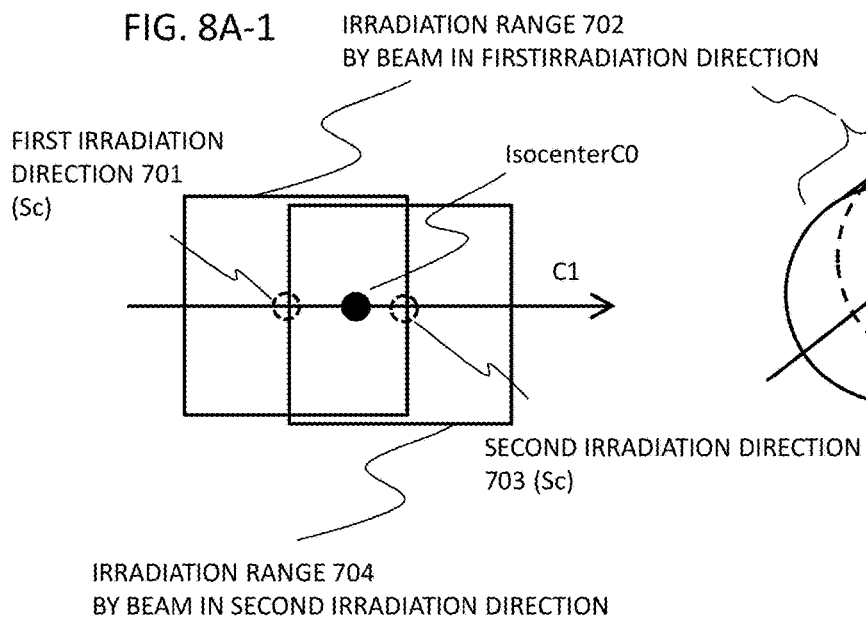
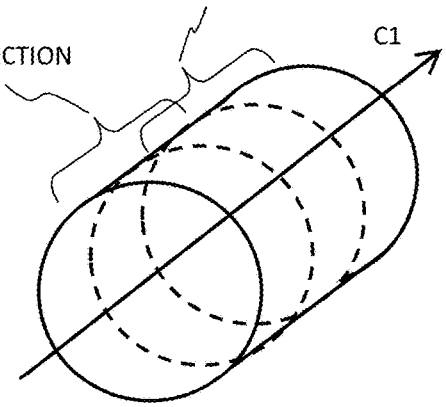
FIG. 8A-1
FIG. 8A-2
IRRADIATION RANGE 704
BY BEAM IN SECOND IRRADIATION DIRECTION
IRRADIATION RANGE 702
BY BEAM IN FIRST IRRADIATION DIRECTION
FIRST IRRADIATION DIRECTION 701 (Sc)
Isocenter C0
SECOND IRRADIATION DIRECTION 703 (Sc)
IRRADIATION RANGE 704
BY BEAM IN SECOND IRRADIATION DIRECTION
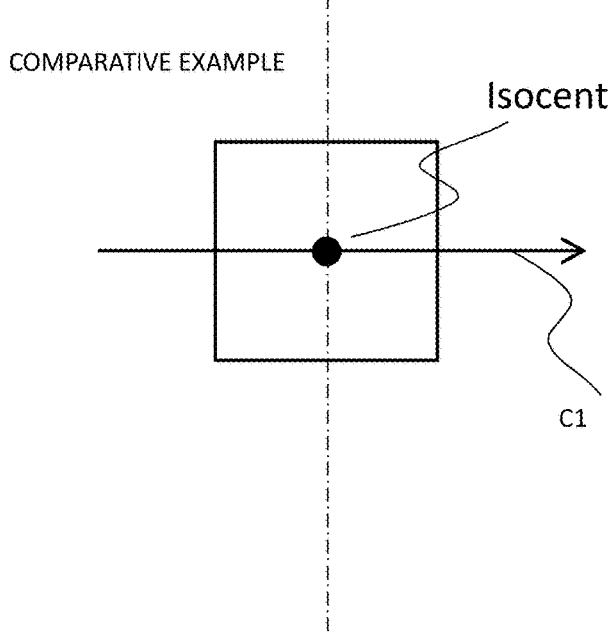
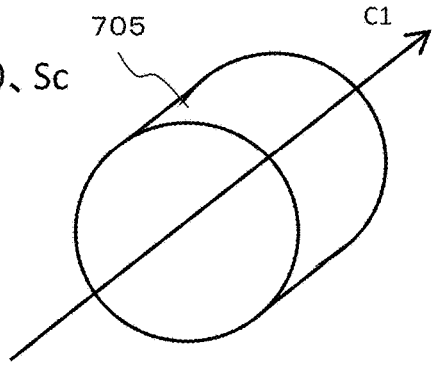
FIG. 8B-1
COMPARATIVE EXAMPLE
Isocenter C0, Sc
FIG. 8B-2
COMPARATIVE EXAMPLE 705

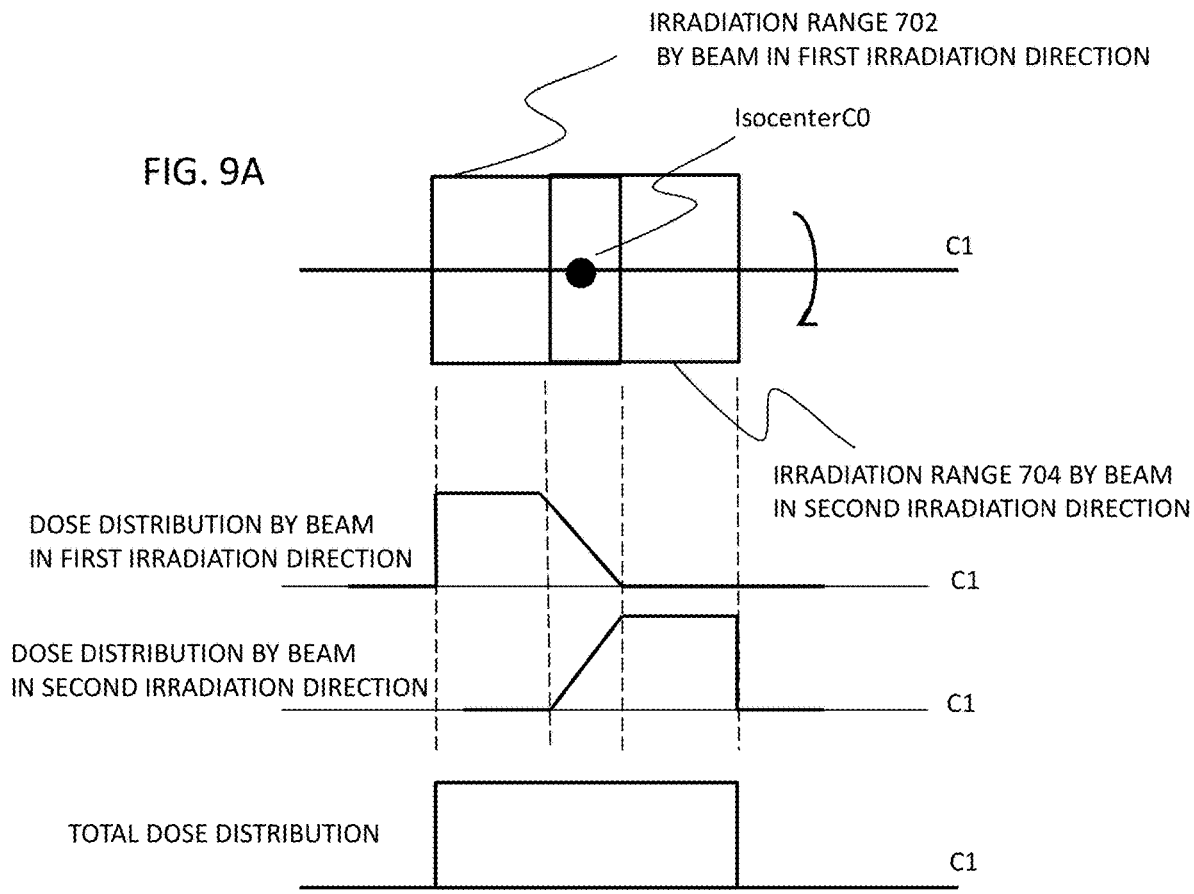
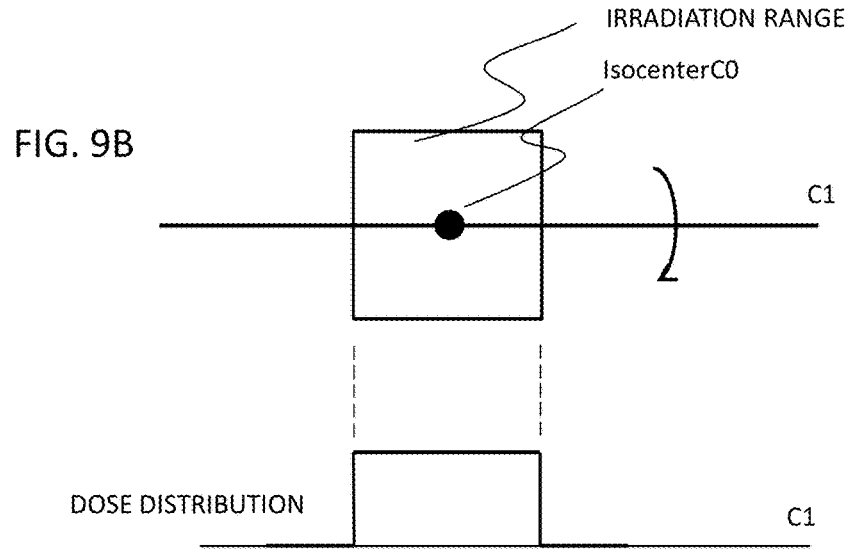

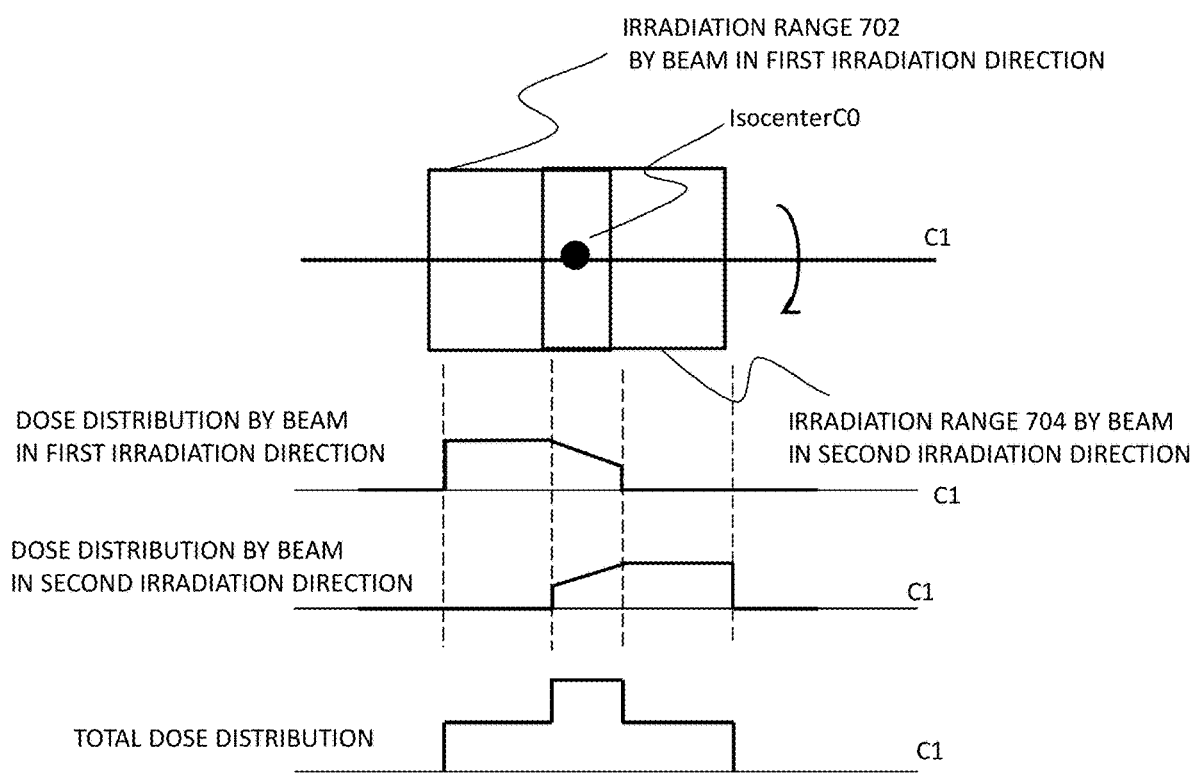

FIG. 13 COMPARATIVE EXAMPLE

RADIATION THERAPY SYSTEM AND METHOD OF OPERATING RADIATION THERAPY APPARATUS

BACKGROUND OF THE INVENTION

1. Field of the Invention

The present invention relates to a radiation therapy apparatus, and more particularly to a radiation therapy apparatus including a multi-leaf collimator that limits a radiation irradiation range to a desired shape.

2. Description of the Related Art

As a radiation therapy method, a method of using a linear accelerator called a linac as a radiation source, and irradiating, with radiation from various directions in three dimensions, an affected area of a patient, which is previously imaged with an X-ray CT device, an MRI device, or the like is used.

For example, an intensity modulated radiation therapy (IMRT) method that uses a multi-leaf collimator (MLC) to shield a part of a radiation beam emitted from the radiation source and irradiate the affected area while modulating a radiation intensity distribution in an area that is irradiated with the radiation, or an intensity-modulated rotating radiation therapy (rotation IMRT) in which the multi-leaf collimator and the radiation are rotated around the patient at that time is known.

In addition, an image-guided radiotherapy (IGRT) method that adjusts an irradiation position of an X-ray that is determined based on an image taken in advance by using a device equipped with an X-ray imaging device in a radiation therapy apparatus, taking an X-ray image immediately before the irradiation with the radiation, and comparing the image with the image taken in advance is also known.

There is also a moving object tracking irradiation method in which when the affected area moves due to a respiratory motion, or the like, a position of the affected area is obtained from the image taken by the X-ray imaging device, a direction of the radiation source is tilted by a gimbal mechanism, and a radiation irradiation direction is made to follow the position of the affected area.

A tomotherapy method is also known in which the intensity-modulated rotating radiation therapy (rotation IMRT) and the image-guided radiotherapy (IGRT) are combined, and a helical irradiation is performed while moving a couch on which the patient is placed.

On the other hand, in order to widen a radiation irradiation range to the patient, JP-A-2008-173182 (Patent Literature 1) provides a method of sequentially irradiating adjacent irradiation ranges with fan beams by inclining a radiation axis from the radiation source at the same position. Further, JP-A-2016-174674 (Patent Literature 2) provides a method of widening the radiation irradiation range by moving an irradiation region by changing the direction of the radiation source while irradiating the irradiation region with the radiation.

It is desired to widen a range in which the patient can be irradiated with the radiation and to increase an irradiation amount of the radiation in the radiation therapy apparatus. As an example, when treating a patient in which small tumors are scattered over a wide area around a large tumor, it becomes possible to irradiate each tumor with the radiation in a short time, which is a great advantage for the patient.

However, in order to widen the radiation irradiation range in the related-art radiation therapy apparatus, it is necessary to arrange a large number of metal thin plates with minute gaps and increase a size of the multi-leaf collimator (MLC) that moves each thin plate, and a weight increases. As the weight of the MLC increases, a deflection occurs in a structure supporting the MLC, and irradiation accuracy decreases. The intensity-modulated rotating radiation therapy, in which the MLC is rotated with the radiation source, and the moving object tracking irradiation method, in which the MLC swings with the radiation source with the gimbal mechanism, also reduce a control response of the swinging and reduce the accuracy due to the deflection of the structure as the weight of the MLC increases.

Further, as in Patent Literature 1, the method of sequentially irradiating the adjacent irradiation ranges with the radiation by inclining the radiation axis from the radiation source at the same position is a process of irradiating one irradiation range, and then stopping the radiation once, directing the radiation source to the adjacent irradiation range by the gimbal mechanism, and performing irradiation with the radiation again, so that the irradiation takes time. In addition, accuracy of an overlap or a gap of irradiation regions depends on accuracy of an angle control of the radiation axis of the gimbal mechanism. Therefore, it is necessary to intermittently and accurately stop the rotation of the gimbal mechanism, which originally supports the weight of the radiation source and the MLC, swings in two orthogonal axes and follows a moving object, and a demand for the gimbal mechanism is increased.

Similarly, in a technique of Patent Literature 2, since it is necessary to accurately change a direction of the radiation axis of the radiation source at a constant speed while performing irradiation with the radiation, a demand for the gimbal mechanism that supports the weight of the radiation source and the MLC is increased.

SUMMARY OF THE INVENTION

An object of the invention is to provide a radiation therapy system capable of widening a radiation irradiation range to a patient without increasing a burden on a structure.

In order to achieve the above object, a radiation therapy apparatus of the invention includes: a radiation source; a rotation mechanism that supports the radiation source and rotates the radiation source around an isocenter; a couch that places a therapy target site of a patient at the isocenter; a head swing mechanism that is disposed between the radiation source and the rotation mechanism and that swings an irradiation axis of a radiation emitted from the radiation source by swinging the radiation source; and a control unit that controls the radiation source, the rotation mechanism, and the head swing mechanism. The control unit holds the head swing mechanism in a state where the irradiation axis of the radiation of the radiation source is shifted from the isocenter in a predetermined direction by a predetermined amount, and rotates the radiation source by the rotation mechanism while emitting the radiation from the radiation source while maintaining the state of the head swing mechanism.

According to the invention, the head swing mechanism is held in a state where the irradiation axis is shifted from the isocenter in the predetermined direction by the predetermined amount, the rotation mechanism is rotated in this state, so that the burden on the structure such as the head swing mechanism and the rotation mechanism is not increased, and the radiation irradiation range to the patient can be widened.

BRIEF DESCRIPTION OF THE DRAWINGS

FIGS. 8A-1 and 8A-2 are illustrative diagrams showing first and second irradiation directions 701 and 703 and irradiation ranges 702 and 704 in the radiation irradiation device of the present embodiment, and FIGS. 8B-1 and 8B-2 are illustrative diagrams showing an irradiation direction and an irradiation range of a comparative example.

FIG. 9A is an illustrative diagram showing dose distributions formed by irradiation of beams in the first and second irradiation directions of the radiation irradiation device of the present embodiment and a total dose distribution thereof, and FIG. 9B is an illustrative diagram showing a dose distribution formed by irradiation of beams of the comparative example.

FIG. 10 is an illustrative diagram showing the dose distributions formed by irradiation of the beams in the first and second irradiation directions of the radiation irradiation device of the present embodiment and the total dose distribution thereof.

DESCRIPTION OF THE PREFERRED EMBODIMENTS

A radiation therapy system according to an embodiment of the invention will be described.

<Apparatus Configuration of Radiation Therapy System>

First, an apparatus configuration of the radiation therapy system of the present embodiment will be described.

Figure 1:
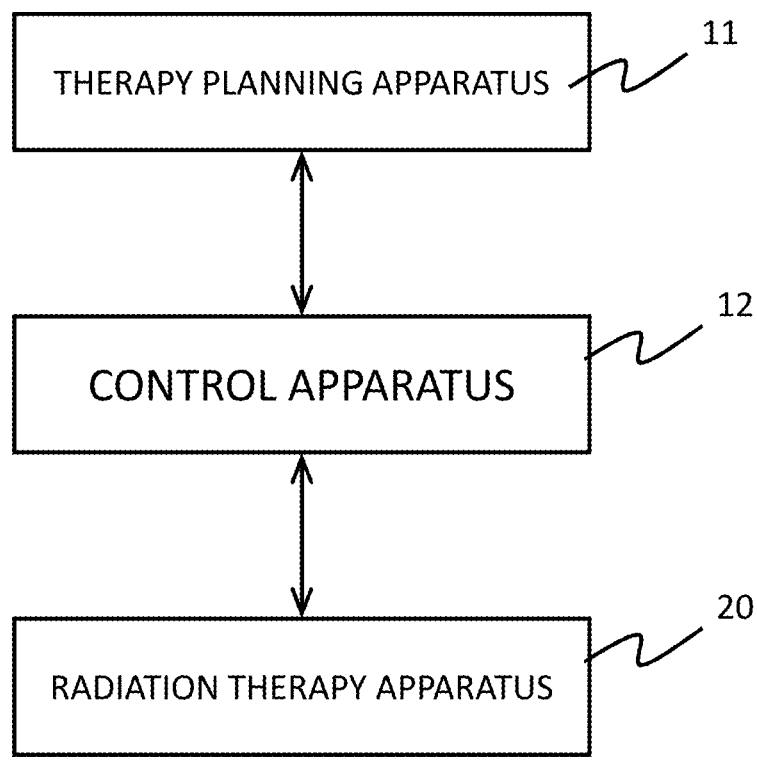
FIG. 1 is a block diagram of a radiation therapy system 10 according to an embodiment of the invention.

As shown in FIG. 1, a radiation therapy system 10 includes a therapy planning apparatus 11, a control apparatus (control unit) 12, and a radiation therapy apparatus 20.

The therapy planning apparatus 11 receives data of a three-dimensional image taken in advance for a patient B, and creates properties (a dose, time, an angle, a position, a radiation region, or the like of radiation emitted to patient B) of the radiation to be emitted to the patient B as a therapy plan according to a content of a radiation therapy. Further, in order to perform irradiation with the radiation according to the dose, the time, the angle, or the like of the radiation of the therapy plan, the therapy planning apparatus 11 outputs, to the control apparatus 12, control parameter values such as atilt angle of a head swing mechanism 301 of a radiation source described later, a rotation angle of a rotating ring 22 with respect to a ring frame 21, a rotation shaft 25 or an irradiation timing of a radiation irradiation device 24.

The control apparatus 12 controls an operation of the radiation therapy apparatus 20 based on the control parameter values received from the therapy planning apparatus 11. The control apparatus 12 includes a CPU and a memory, and the CPU reads and executes a program stored in the memory in advance to execute a control operation by software.

Figure 2:
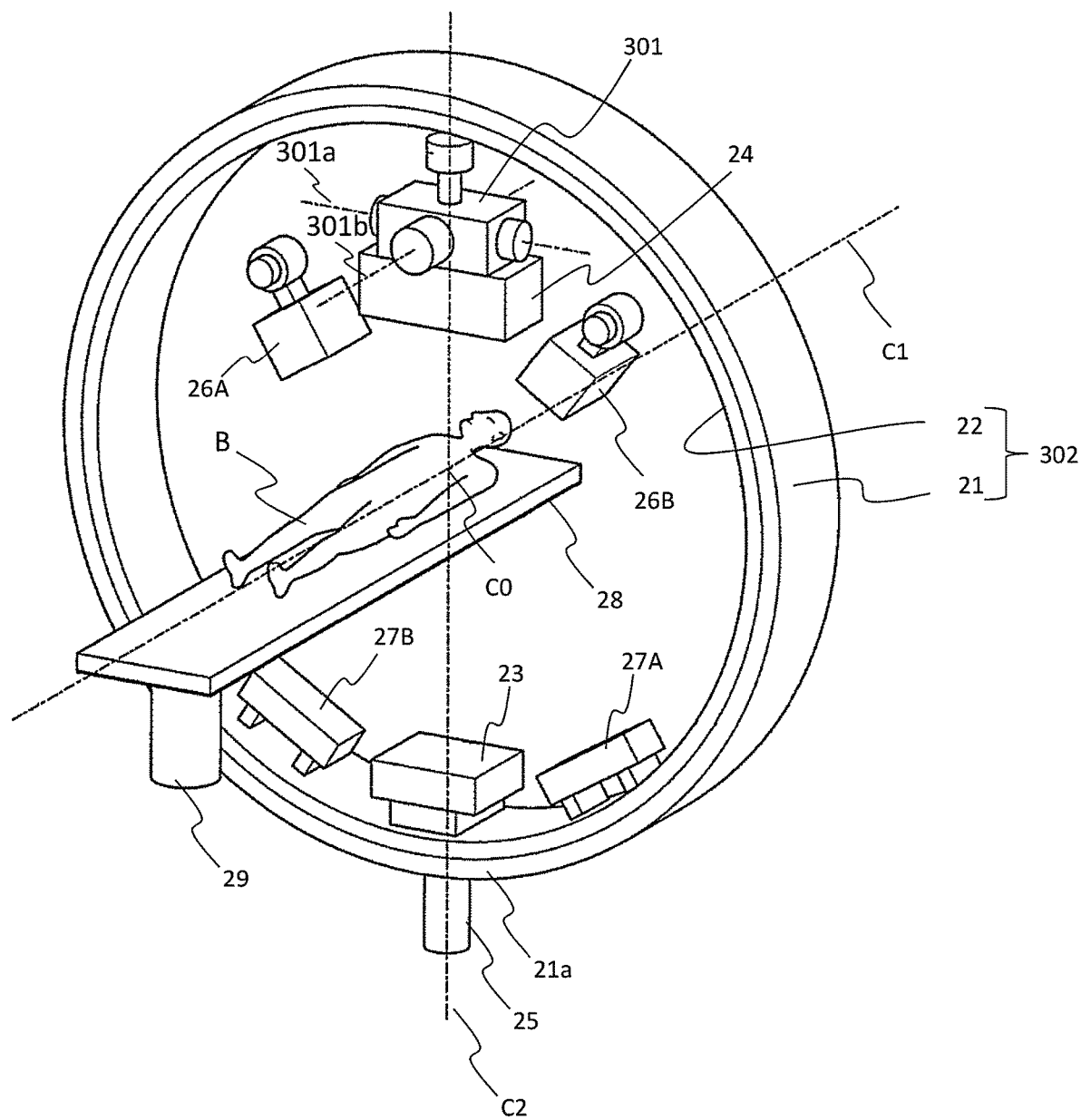
FIG. 2 is a perspective view of a radiation therapy apparatus 20 of the present embodiment.

FIG. 2 is a perspective view showing a schematic configuration of the radiation therapy apparatus 20.

As shown in FIG. 2, the radiation therapy apparatus 20 includes the radiation irradiation device 24, a rotation mechanism 302, a couch 28, and the head swing mechanism 301. The rotation mechanism 302 supports the radiation irradiation device 24 and rotates a radiation source 50 around an isocenter C0. The couch 28 places a therapy target site of the patient at the isocenter C0. The head swing mechanism 301 is disposed between the radiation irradiation device 24 and the rotation mechanism 302, and swings an irradiation axis of the radiation emitted by the radiation irradiation device 24 by swinging the radiation irradiation device 24.

The rotation mechanism 302 includes the ring frame 21 and the rotation ring 22.

The ring frame 21 is disposed such that a rotation central axis C1 faces a substantially horizontal direction. The rotating ring 22 has a structure in which an outer peripheral surface thereof is supported by an inner peripheral surface of the ring frame 21 and can rotate along the inner peripheral surface of the ring frame 21. The rotating ring 22 is driven by a rotation drive mechanism (not shown) and rotates around the rotation central axis C1.

The rotation shaft 25 extending downward is integrally formed on the outer peripheral surface of a lower end portion 21a of the ring frame 21, and the rotation shaft 25 is supported by a base (not shown) in a state in which the rotation shaft 25 can rotate (swivel) around a vertical central axis (swivel axis) C2 thereof. A swivel drive mechanism (not shown) swivels the ring frame 21 around the swivel axis C2.

Figure 3:
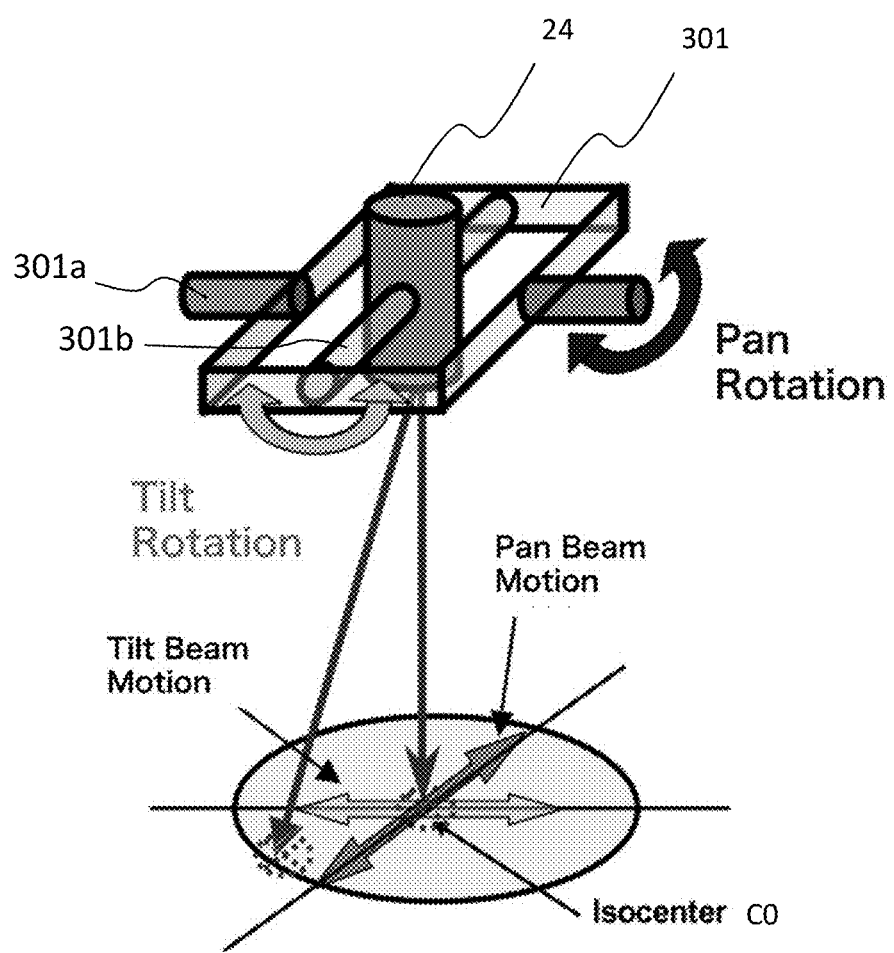
FIG. 3 is an illustrative view showing a schematic configuration of a head swing mechanism 301 in the radiation therapy apparatus 20 of FIG. 2.

As shown in FIG. 3, the radiation irradiation device 24 is mounted on the head swing mechanism 301 having a gimbal structure, and is supported by the rotating ring 22 via the head swing mechanism 301.

When the head swing mechanism 301 does not operate, radiation Sr emitted from the radiation irradiation device 24 is adjusted so as to pass through the isocenter C0, which is an intersection of the rotation central axis C1 of the rotating ring 22 and the swivel axis C2 of the ring frame 21.

The radiation therapy apparatus 20 further includes a sensor array 23. The sensor array 23 receives the radiation emitted from the radiation irradiation device 24 and transmitted through a subject around the isocenter C0, and generates a transmission image of the subject. As the sensor array 23, a flat panel detector (FPD), an X-ray image intensifier (II), or the like can be used.

Further, the radiation therapy apparatus 20 includes imaging x-ray sources 26A and 26B and sensor arrays 27A and 27B. The imaging X-ray sources 26A and 26B and the sensor arrays 27A and 27B are disposed on an inner peripheral side of the rotating ring 22 and supported by the rotating ring 22. The imaging X-ray sources 26A and 26B are directed to emit an imaging X-ray 101 toward the isocenter C0. The imaging X-ray 101 is a conical cone beam. The sensor arrays 27A and 27B are disposed at positions facing the imaging X-ray sources 26A and 26B with the isocenter C0 in between, receive the imaging X-rays 101 emitted from the imaging X-ray sources 26A and 26B and transmitted through the subject around the isocenter C0, and generate the transmission image of the subject. As the sensor arrays 27A and 27B, for example, the FPD, the X-ray II, or the like can be used.

A couch driving device 29 can be controlled by the control apparatus 12 to move the couch 28 in parallel with at least the rotation central axis C1.

The head swing mechanism 301 has the gimbal structure equipped with the radiation irradiation device 24, and the radiation irradiation device 24 can be tilted around two shafts of a pan shaft 301a and a tilt shaft 301b. The pan shaft 301a is a shaft perpendicular to both the rotation central axis C1 and the swivel axis C2. The tilt shaft 301b is a shaft parallel to the rotation central axis C1.

Figure 4:
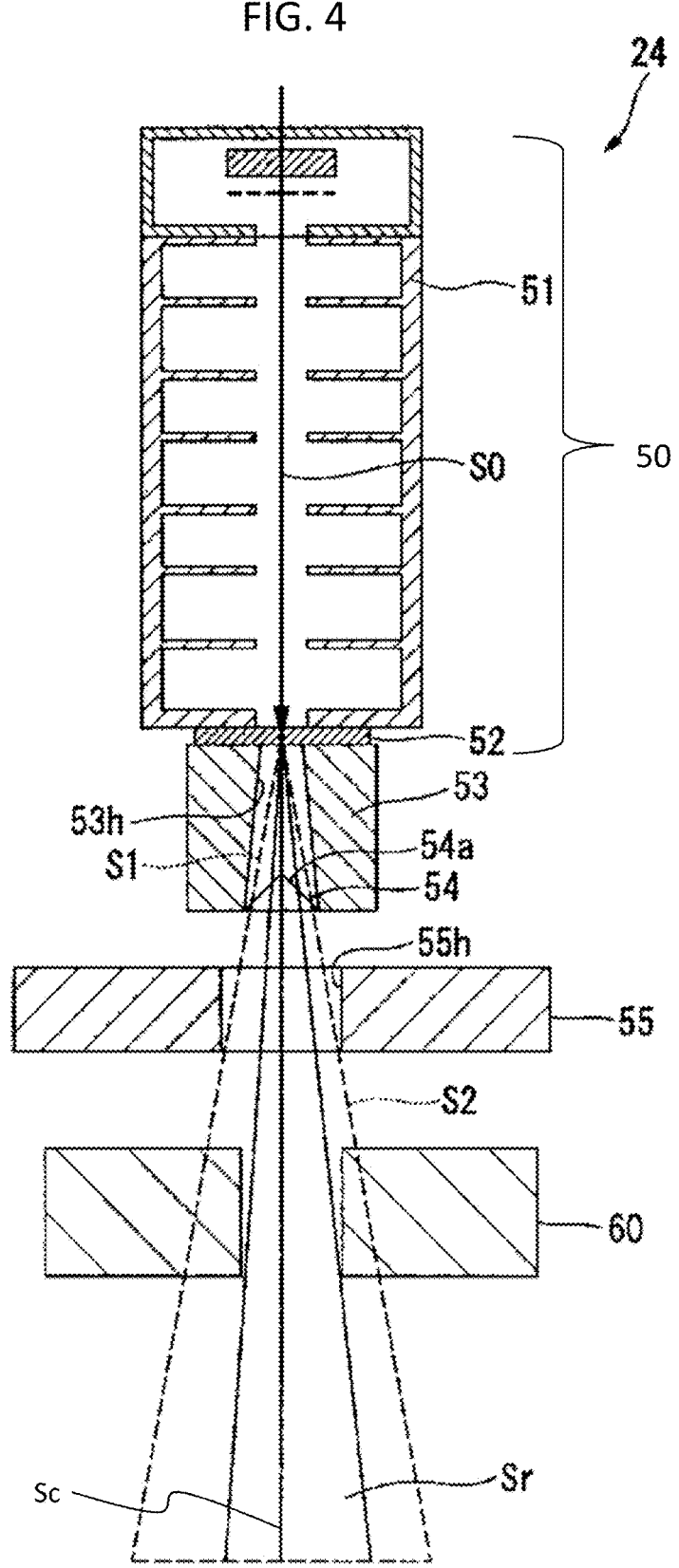
FIG. 4 is a cross-sectional view of a radiation irradiation device 24 of FIG. 3.

As shown in FIG. 4, the radiation irradiation device 24 includes the radiation source 50, a primary collimator 53, a flattening filter 54, a secondary collimator 55, and a multi-leaf collimator (MLC) 60.

Here, the radiation source 50 is an X-ray source including an electron beam accelerator 51 and an X-ray target 52. The electron beam accelerator 51 irradiates the X-ray target 52 with an electron beam S0 generated by accelerating electrons. The X-ray target 52 is made of tungsten, a tungsten alloy, or the like. The X-ray target 52 emits radiation S1 when irradiated with the electron beam S0.

The primary collimator 53 and the secondary collimator 55 are made of X-ray shields (lead, the tungsten, or the like) including through holes 53h and 55h, respectively, shield a part of the radiation S1 and emit the radiation S1 that has passed through the through holes 53h and 55h.

The flattening filter 54 includes a conical protrusion 54a made of aluminum or the like, and is disposed on an outlet side of the through hole 53h of the primary collimator 53. The flattening filter 54 makes a dose distribution of the radiation S1 uniform in a plane perpendicular to a radiation direction of the radiation S1.

After passing through the primary collimator 53, the flattening filter 54, and the secondary collimator 55, radiation S2 having a uniform intensity distribution is incident on the multi-leaf collimator 60. The multi-leaf collimator 60 is controlled by the control apparatus 12 to limit an irradiation field of the radiation S2.

Figure 7:
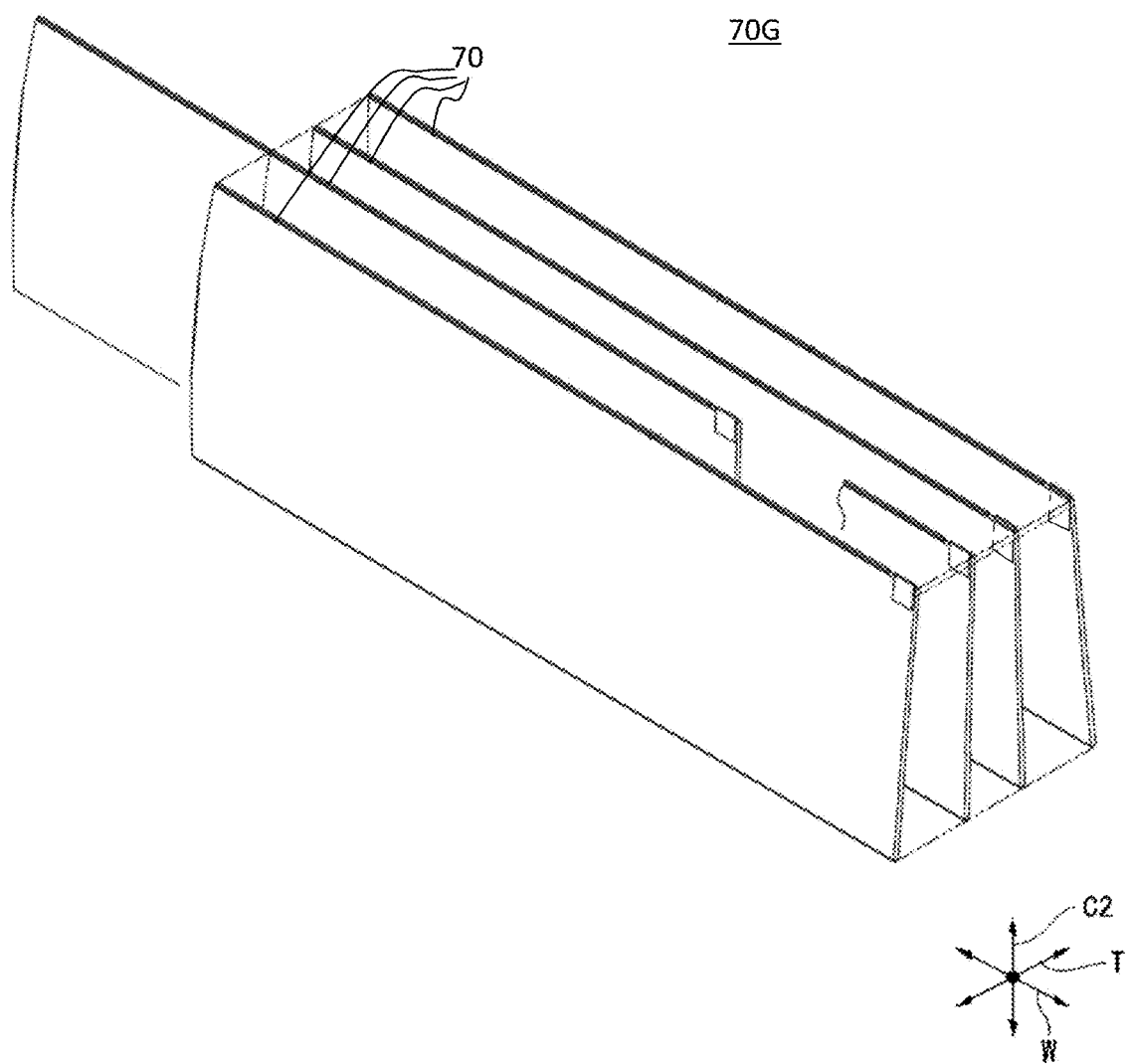
FIG. 7 is a perspective view showing a configuration example of a leaf group 70G of a multi-leaf collimator 60 of FIG. 4.

As shown in FIG. 7, the multi-leaf collimator 60 has a structure in which two sets of leaf groups 70G in which a plurality of leaves (thin plates) 70 made of a material (the lead, the tungsten, or the like) that shields the radiation are arranged in a thickness direction are opposed to each other, and a main plane of the leaves 70 is substantially parallel to the irradiation axis of the radiation. Under control of the control apparatus 12, a driving unit projects or retracts each leaf in a direction that shields the irradiation axis of the radiation, so that the irradiation field of the radiation S2 can be limited or the dose distribution of the radiation in the irradiation field can be modulated.

<Operation of Radiation Therapy System>

Hereinafter, in the radiation therapy system of the present embodiment, when a therapy is performed by irradiating the patient with the radiation, an operation of the therapy in an irradiation range expansion mode will be described.

In the irradiation range expansion mode, the control apparatus 12 holds the head swing mechanism 301 in a state where an irradiation axis Sc of the radiation of the radiation source is shifted from the isocenter C0 in a predetermined direction by a predetermined amount, and rotates the radiation source 50 (the radiation irradiation device 24) by the rotation mechanism 302 while emitting the radiation from the radiation source while maintaining the state of the head swing mechanism.

Figure 5:
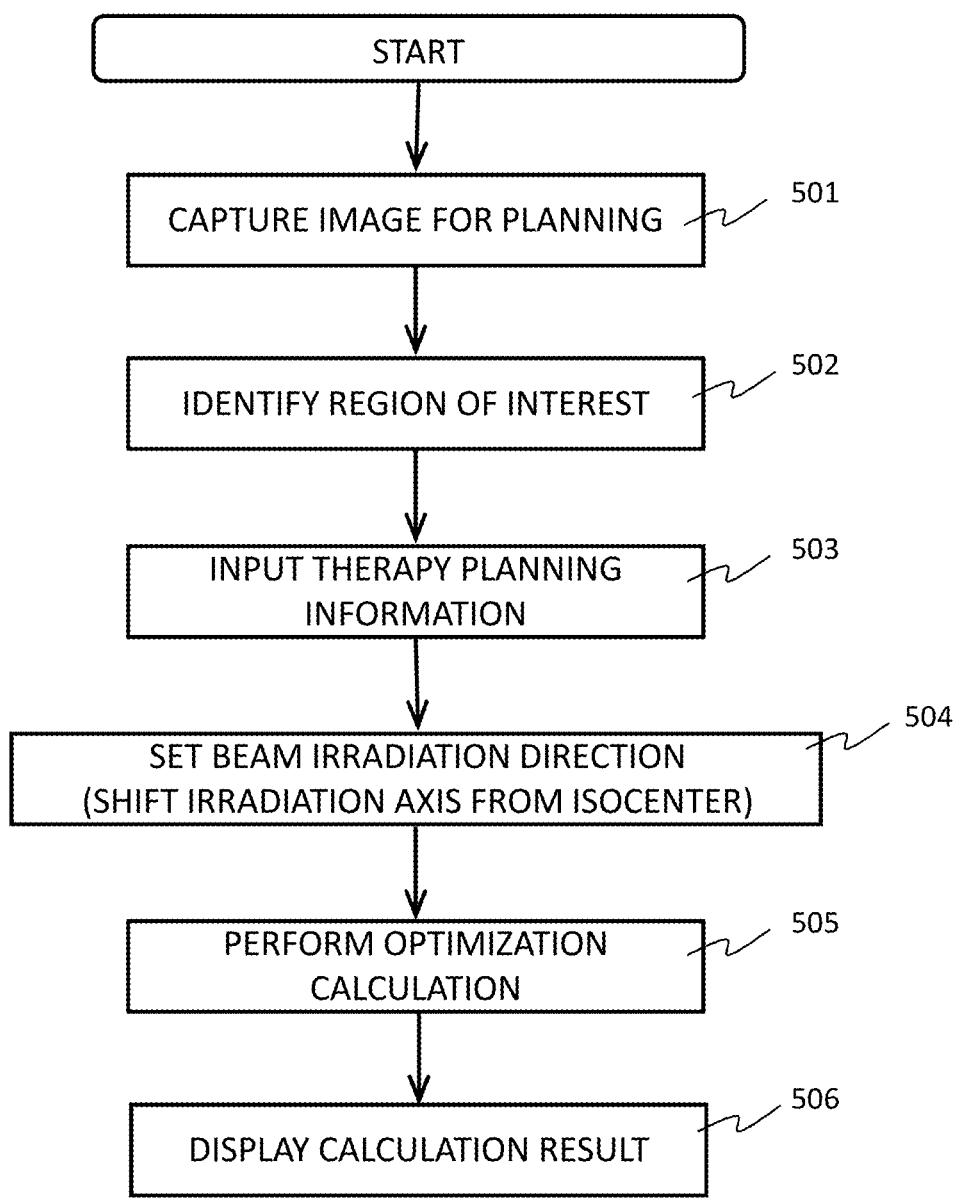
FIG. 5 is a flowchart showing an operation of the radiation therapy system of the present embodiment.

First, as shown in a flow of FIG. 5, the therapy planning apparatus 11 captures data of the three-dimensional image for the therapy plan taken in advance for the patient B (step 501). The therapy planning apparatus 11 sets a region of interest such as a region to be irradiated with the radiation or a region to be avoided by extracting a region from a three-dimensional image by image processing, or receiving identification of the region from a user (step 502). Next, the therapy planning apparatus 11 receives information necessary for the therapy plan such as a dose of the radiation to be emitted for each region of interest or a maximum allowable radiation dose from the user (step 503), and creates the dose, the time, the angle, the position, the radiation region, or the like of the radiation to be emitted to the patient B as the therapy plan. Further, by performing an optimization calculation that takes into consideration an irradiation dose rate of the radiation therapy apparatus or an operating range of each machine operating axis, an optimum intensity distribution of the radiation that can be emitted by the radiation therapy apparatus and satisfies a radiation dose constraint of each region of interest is obtained by a calculation (step 505). For each machine operating axis at this time, each leaf drive shaft of the MLC, rotation of the rotating ring 21 around the rotation central axis C1, swivel of the ring frame 21 around the swivel axis C2, or the like are selected and used.

In steps 504 and 505, the therapy planning apparatus 11 determines an amount and a direction of shifting the irradiation axis Sc of the radiation of the radiation source from the isocenter C0 by the head swing mechanism 301, and also calculates a parameter value of a control signal for rotating the radiation source 50 (the radiation irradiation device 24) by the rotation mechanism 302 while emitting the radiation from the radiation source 50 while maintaining the state of the head swing mechanism 301, and a parameter value of the control signal that operates opening and closing of each leaf of the MLC 60 for realizing the optimum intensity distribution of the radiation at that time.

The therapy planning apparatus 11 displays a result of an obtained therapy plan to the user (step 506).

The control apparatus 12 irradiates the patient with the radiation as follows by receiving the parameter value of the control signal calculated by the therapy planning apparatus 11 to realize the therapy plan, and controlling the head swing mechanism 301, the rotation angle of the rotating ring 22, and the opening and closing of the leaf of the MLC 60.

Figure 6:
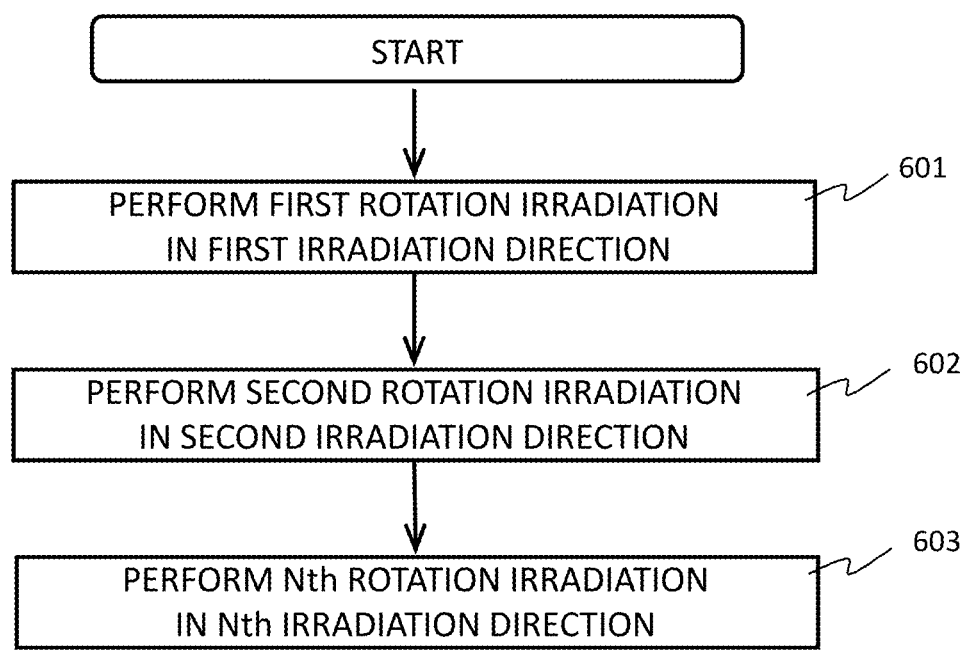
FIG. 6 is a flowchart showing an operation of the radiation therapy system of the present embodiment.

Specifically, as in step 601 of a flow of FIG. 6, the control apparatus 12 rotates the pan shaft 301a and/or the tilt shaft 301b of the head swing mechanism 301, sets the radiation irradiation axis Sc of the radiation irradiation device 24 to a first irradiation direction 701 shifted by the predetermined amount from the isocenter C0, and rotates the radiation source 50 (the radiation irradiation device 24) by the rotation mechanism 302 by a predetermined angle range (here, 360 degrees) while emitting the radiation from the radiation source 50 while maintaining the state (step 601). At this time, while the radiation source 50 is rotated, the control apparatus 12 operates the MLC 60 to generate the intensity distribution in the radiation beam.

Accordingly, for example, when the first irradiation direction 701 is set on the rotation central axis C1 by the rotation of the pan shaft 301a as shown in FIG. 8A-1, a cylindrical irradiation range 702 is irradiated with the radiation as shown in FIG. 8A-2.

Next, as in step 602, the control apparatus 12 rotates the pan shaft 301a and/or the tilt shaft 301b of the head swing mechanism 301, sets the radiation irradiation axis Sc of the radiation irradiation device 24 to a second irradiation direction 703 shifted by the predetermined amount from the isocenter C0, and rotates the radiation source 50 (the radiation irradiation device 24) by the rotation mechanism 302 by the predetermined angle range (here, 360 degrees) while emitting the radiation from the radiation source 50 while maintaining the state (step 602). At this time, while the radiation source 50 is rotated, the control apparatus 12 operates the MLC 60 to generate the intensity distribution in the radiation beam. At this time, rotation time of the rotation mechanism can be further shortened when a direction is opposite to the first irradiation direction. Alternatively, in a case of a helical scan type, the radiation source 50 may be set to rotate in the second irradiation direction 703 while rotating by the rotation mechanism in the same direction as the first irradiation direction.

Accordingly, when the direction in which the second irradiation direction 703 is shifted as shown in FIG. 8A-1 is set to be opposite to the first irradiation direction 701 (a negative direction of the rotation central axis C1), a cylindrical irradiation range 704 is irradiated with the radiation as shown in FIG. 8A-2.

The processing is repeated N times according to the therapy plan (step 603).

Accordingly, as compared with an irradiation range 705 formed when the radiation source 50 is rotated by the rotation mechanism 302 with the radiation irradiation axis Sc directed to the isocenter C0 as in a comparative example, in the present embodiment, a total range of the irradiation ranges 702 and 703 is irradiated. Therefore, the radiation irradiation range can be efficiently widened.

Further, in the above operation of the present embodiment, once the head swing mechanism 301 holding the MLC 60 that is large in weight and the radiation source 50 is directed to the first irradiation direction 701 or the second irradiation direction 703, the radiation source 50 may be rotated by the rotating mechanism 302 while maintaining the direction, and a burden of the head swing mechanism 301 is small. Therefore, irradiation accuracy is unlikely to be lowered due to a deflection of the head swing mechanism 301, and the affected area can be irradiated with the radiation with high accuracy.

Further, as shown in FIG. 8A-1, the therapy plan can be set such that the irradiation range 702 by the radiation beam in the first irradiation direction 701 and the irradiation range 704 by the radiation beam in the second irradiation direction 703 (that is, an angular range of a radiation spread angle) each includes the isocenter C0. In this case, an overlapping range is generated between the irradiation range 702 and the irradiation range 704. By generating a desired dose distribution in this overlapping range by the MLC 60, the dose distribution of a total irradiation range of the irradiation ranges 702 and 704 can be designed to a desired distribution.

For example, as shown in FIG. 9A, the total dose distribution in a direction of the rotation central axis C1 can be flattened by gradually decreasing and gradually increasing the dose distributions in the overlapping range of the irradiation ranges 702 and 704 in the direction of the rotation central axis C1. Accordingly, a flat dose distribution can be obtained as shown in FIG. 9A even in an enlarged irradiation range as in a case where the irradiation axis Sc of the radiation is aligned with the isocenter C0 of the comparative example of FIG. 9B.

Further, as shown in FIG. 10, by changing a degree of the gradual decrease and the gradual increase of the dose distributions in the direction of the rotation central axis C1 in the overlapping range of the irradiation ranges 702 and 704, the total dose around the isocenter C0 can also be higher than that in the surroundings. Accordingly, it is possible to irradiate a tumor located in the isocenter with a higher dose than that located in the surroundings.

Figure 11:
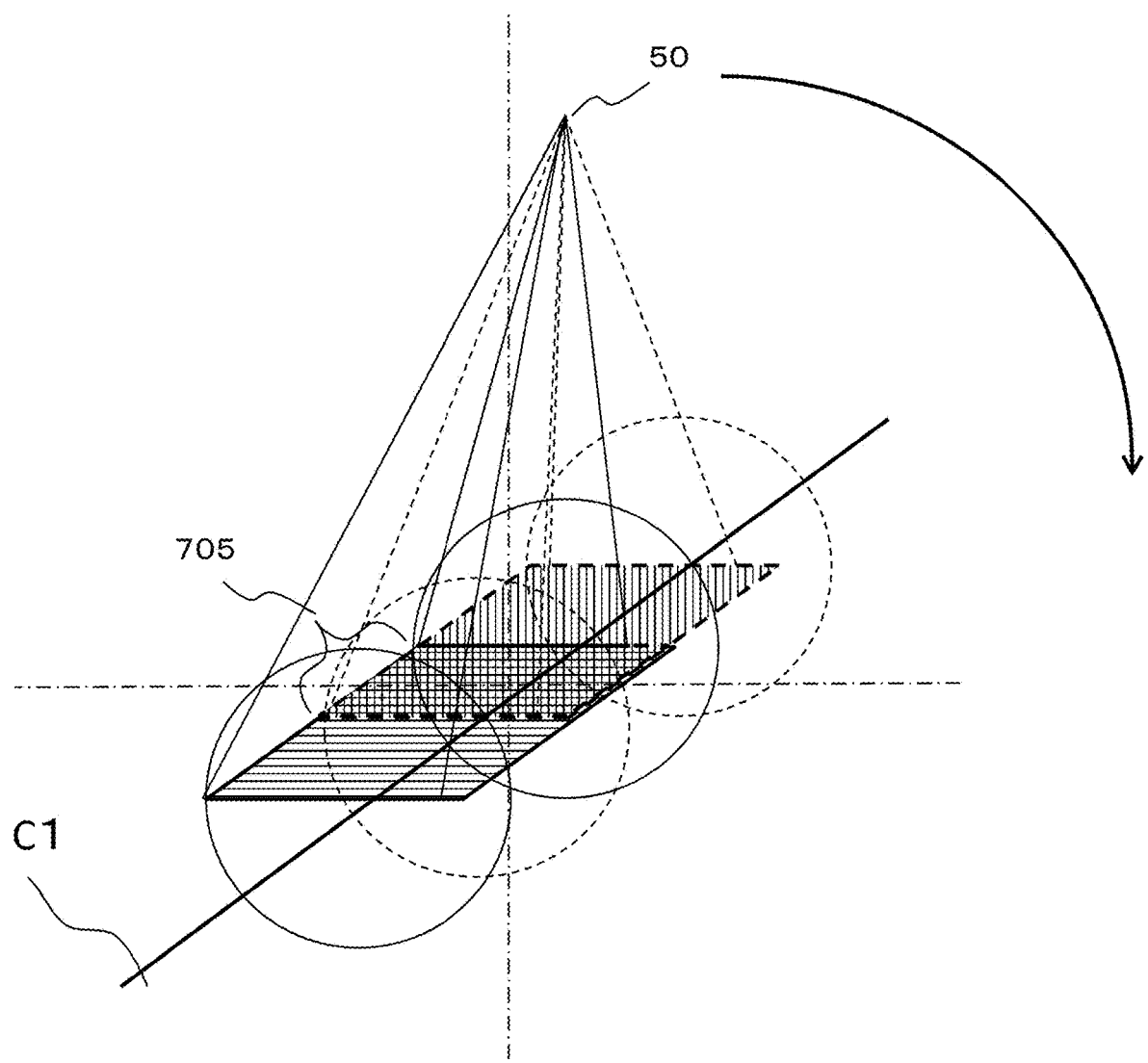
FIG. 11 is an illustrative diagram showing an overlap of irradiation ranges of the radiation irradiation device of the present embodiment.

That is, as shown in FIG. 11, a complicated dose distribution can be generated in the overlapping range 705 of the irradiation ranges 702 and 704.

<Example of Expanding Irradiation Range in Rotation Radial Direction of Rotation Mechanism 302>

In FIGS. 8A-1 to 8B-2, FIGS. 9A and 9B, FIGS. 10 and 11 described above, an example of expanding the irradiation range in the direction of the rotation central axis C1 is shown, but in the present embodiment, the irradiation range can also be expanded in a rotation radial direction.

Figure 12:
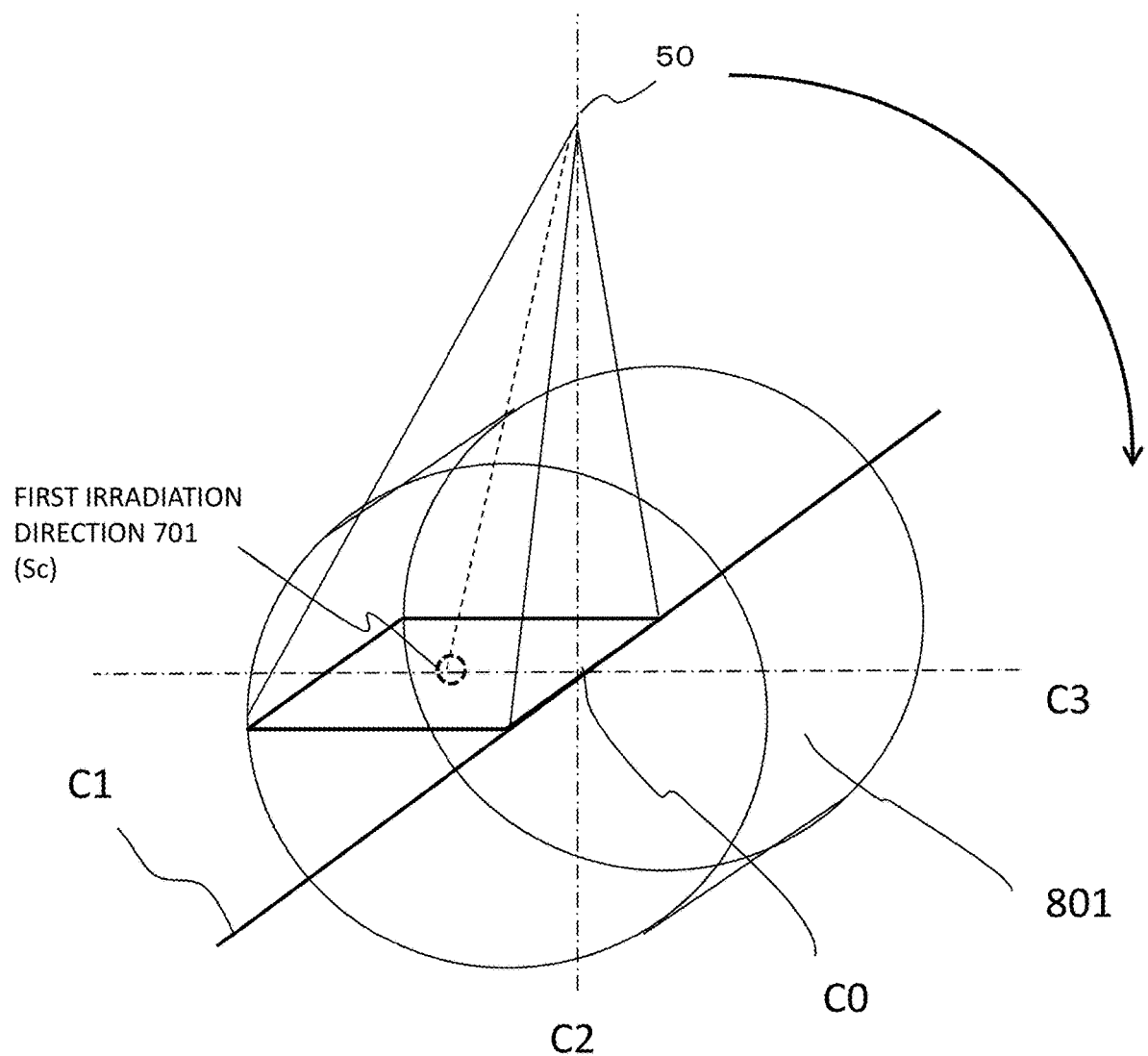
FIG. 12 is an illustrative diagram showing an irradiation range when the first irradiation direction of the radiation irradiation device of the present embodiment is shifted in a radial direction.

Specifically, as shown in FIG. 12, the control apparatus 12 rotates the tilt shaft 301b of the head swing mechanism 301, shifts the radiation irradiation axis Sc in the direction of an axis C3 orthogonal to the rotation central axis C1 and the swivel axis C2, and sets the first irradiation direction 701. The radiation source 50 (the radiation irradiation device 24) is rotated by the rotation mechanism 302 by the predetermined angle range (here, 360 degrees) while emitting the radiation from the radiation source 50 while maintaining the state (step 601). At this time, while the radiation source 50 is rotated, the control apparatus 12 operates the MLC 60 to generate the intensity distribution in the radiation beam.

Figure 13:
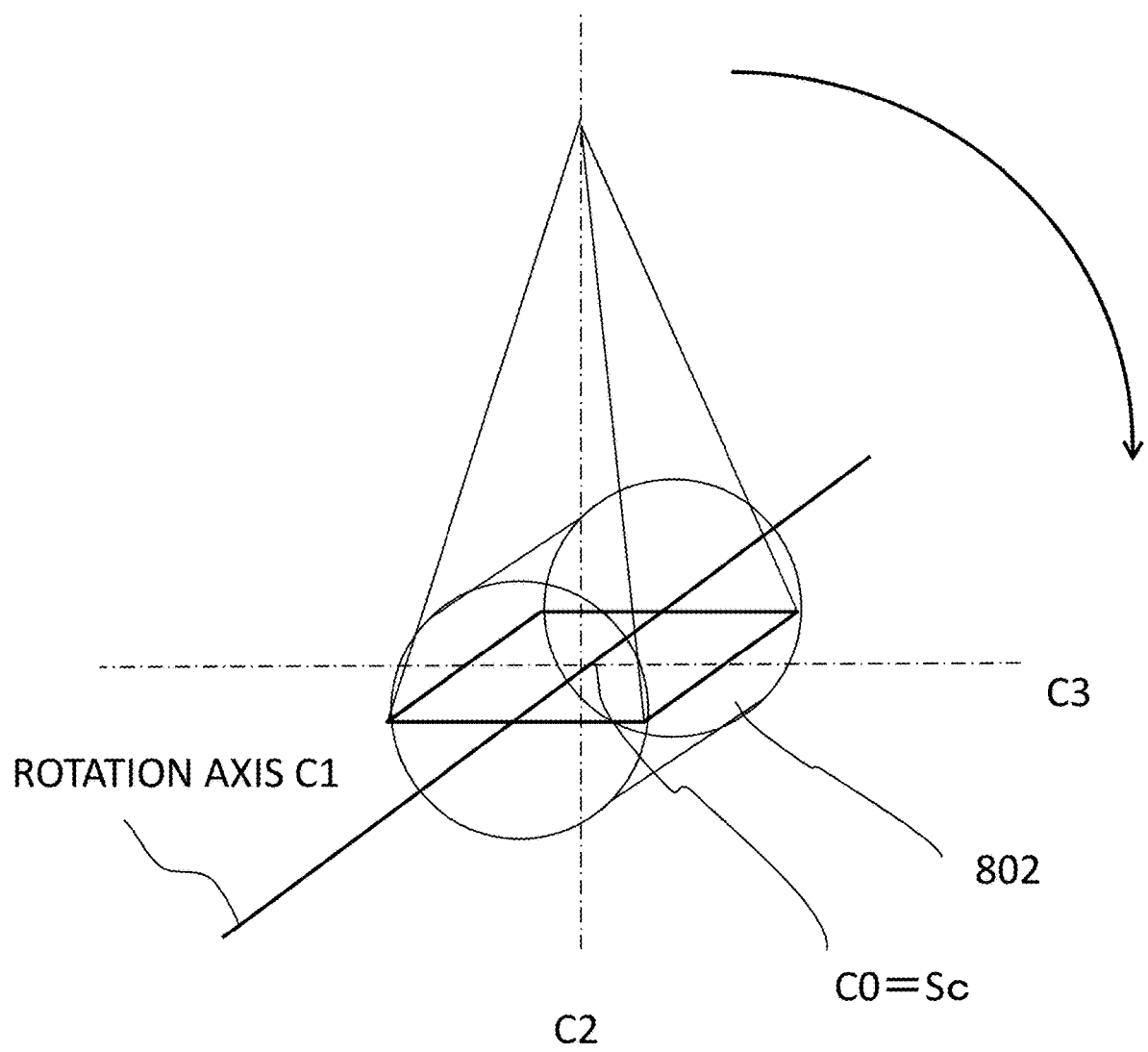
FIG. 13 is an illustrative diagram showing the irradiation range of the comparative example.

Accordingly, a cylindrical irradiation range 801 is irradiated with the radiation as shown in FIG. 12. The irradiation range 801 of FIG. 12 has a radius twice as large as that of an irradiation range 802 when the radiation irradiation axis Sc is aligned with the isocenter C0 as shown in FIG. 13, which is the comparative example, and the irradiation range is expanded. In addition, since the burden of the head swing mechanism 301 is small, the irradiation accuracy is unlikely to be lowered due to the deflection of the head swing mechanism 301, and the affected area can be irradiated with the radiation with the high accuracy.

<Example of Expanding Irradiation Range in Rotation Axis Direction and Rotation Radial Direction of Rotation Mechanism 302>

Figure 14:
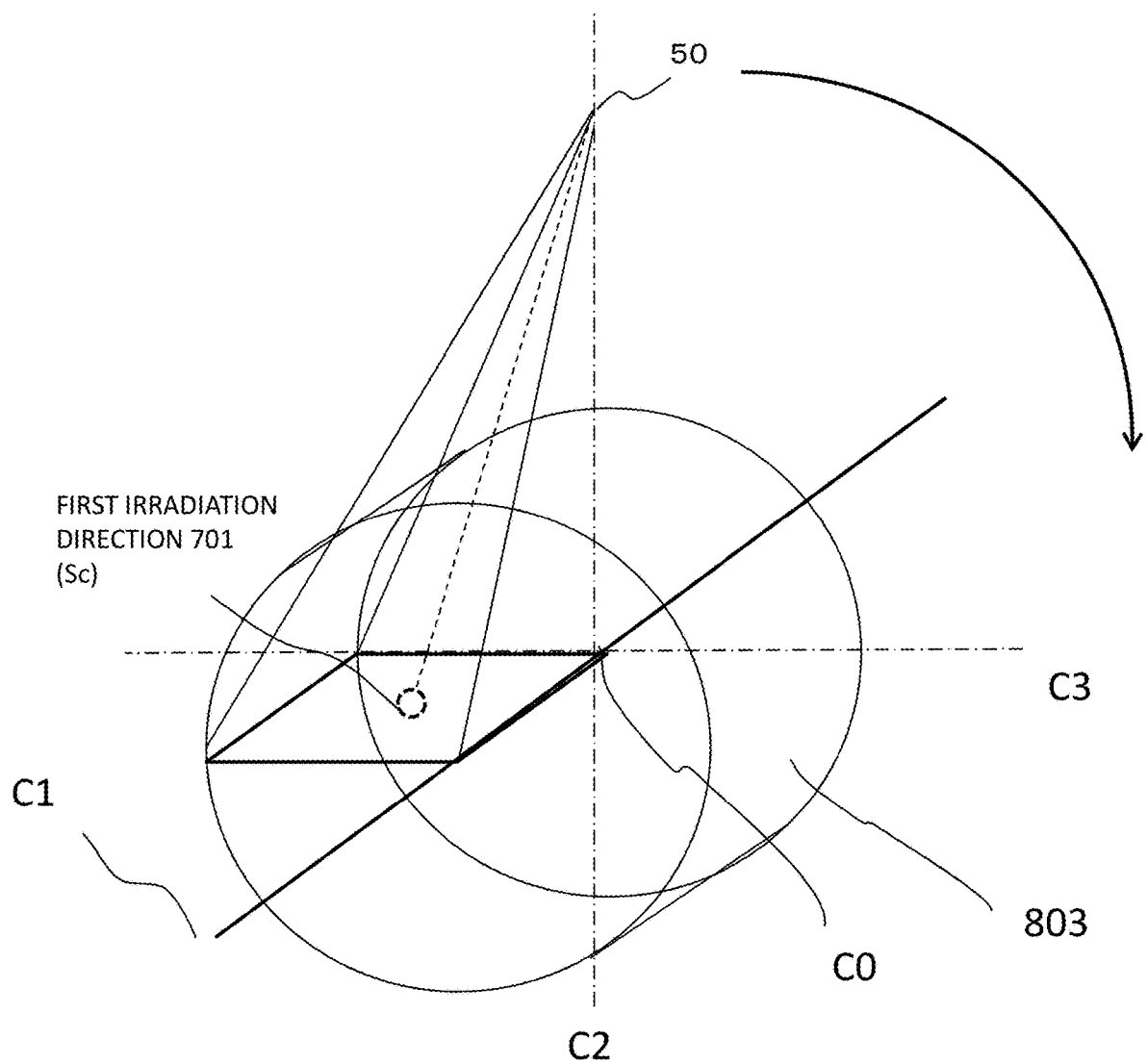
FIG. 14 is an illustrative diagram showing an irradiation range when the first irradiation direction of the radiation irradiation device of the present embodiment is shifted in the radial direction and a rotation axis direction.

As shown in FIG. 14, the control apparatus 12 rotates both the pan shaft 301a and the tilt shaft 301b of the head swing mechanism 301, shifts the radiation irradiation axis Sc in the direction of the rotation central axis C1 and the axis C3, and sets the first irradiation direction 701. The radiation source 50 (the radiation irradiation device 24) is rotated by the rotation mechanism 302 by the predetermined angle range (here, 360 degrees) while emitting the radiation from the radiation source 50 while maintaining the state (step 601). At this time, while the radiation source 50 is rotated, the control apparatus 12 operates the MLC 60 to generate the intensity distribution in the radiation beam.

Accordingly, a cylindrical irradiation range 803 is irradiated with the radiation as shown in FIG. 14. The irradiation range 803 of FIG. 14 has an expanded irradiation range in the radial direction.

Figure 15:
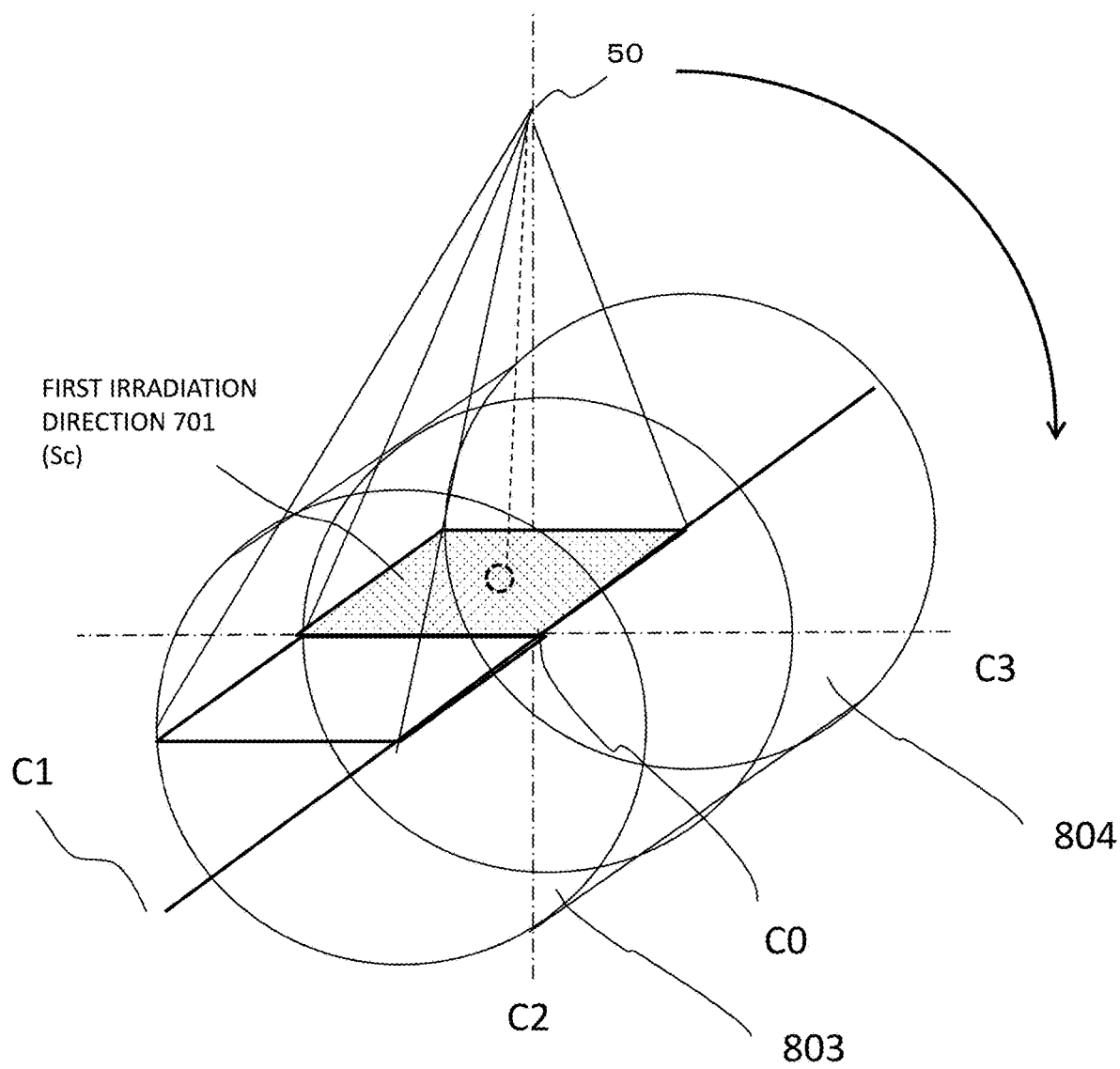
FIG. 15 is an illustrative diagram showing an irradiation range when the second irradiation direction of the radiation irradiation device of the present embodiment is shifted in the radial direction and the rotation axis direction.

Next, as shown in FIG. 15, the control apparatus 12 rotates both the pan shaft 301a and the tilt shaft 301b of the head swing mechanism 301, shifts the radiation irradiation axis Sc in the directions of the rotation central axis C1 and the axis C3, and sets the second irradiation direction 703. In the second irradiation direction 703, the rotation direction of the pan shaft 301a of the head swing mechanism 301 is opposite to that in the case of FIG. 14. The radiation source 50 (the radiation irradiation device 24) is rotated by the rotation mechanism 302 by the predetermined angle range (here, 360 degrees) while emitting the radiation from the radiation source 50 while maintaining the state (step 602). At this time, while the radiation source 50 is rotated, the control apparatus 12 operates the MLC 60 to generate the intensity distribution in the radiation beam.

Accordingly, as shown in FIG. 15, a cylindrical irradiation range 804 expanded twice in the radial direction is irradiated with the radiation.

Figure 16:
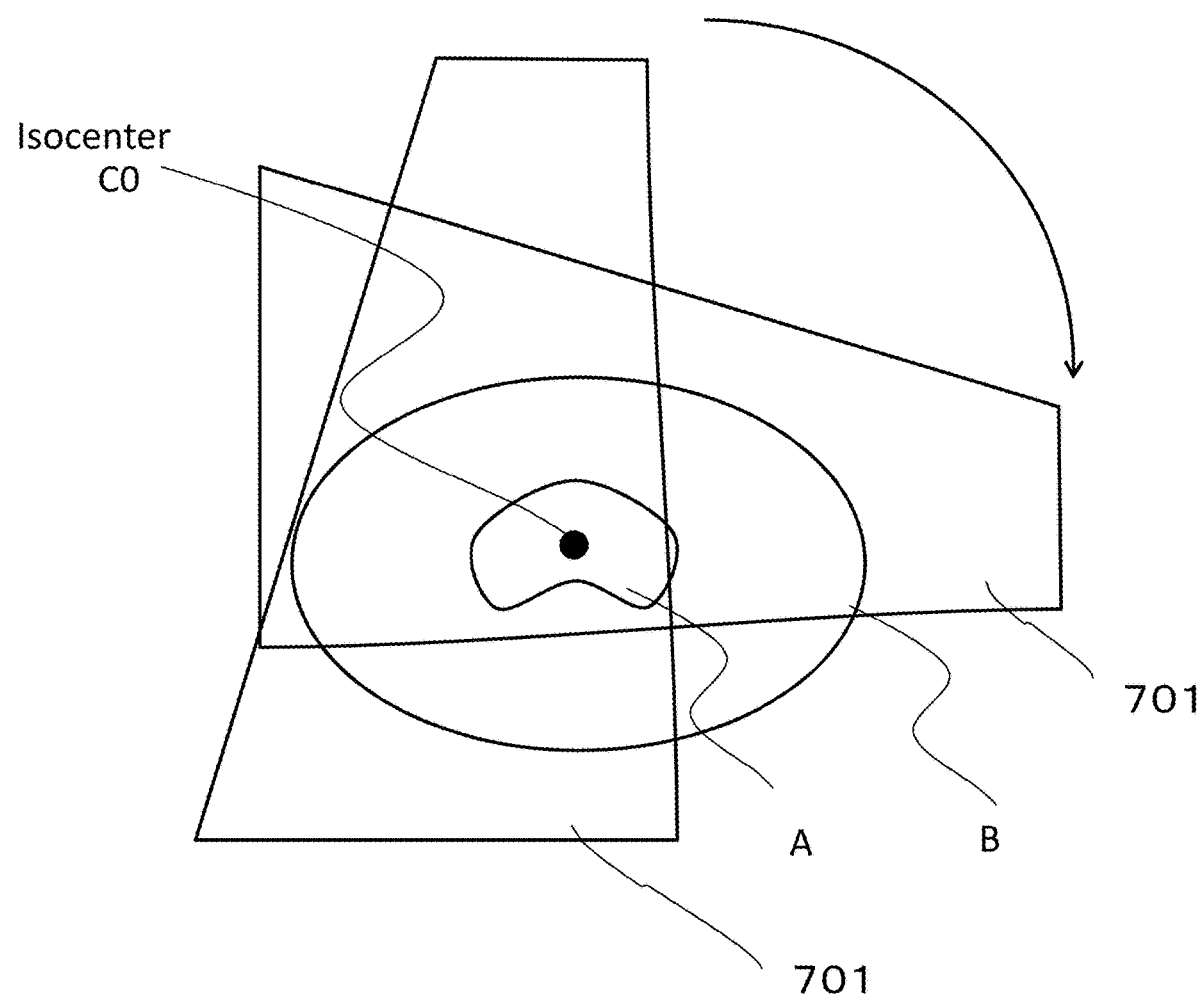
FIG. 16 is an illustrative diagram showing that when the irradiation direction is shifted in the radial direction so as to include an isocenter in the irradiation range of the radiation irradiation device of the present embodiment, the dose distribution in a vicinity of the isocenter is larger than that in surroundings.

Further, in the examples of FIGS. 12, 14, and 15, the irradiation directions 701 and 703 shifted by the head swing mechanism 301 do not include the isocenter C0, but as shown in FIG. 16, it is needless to say that the irradiation direction 701 can be set so as to include the isocenter C0. In this case, when the rotation mechanism 302 rotates the radiation source 50 by 360 degrees, the irradiation range 702 is doubled in the isocenter C0 and the vicinity thereof, so that the total dose of a tumor A in the vicinity of the isocenter C0 becomes larger than that in a surrounding B. Therefore, similar to the total dose distribution shown in FIG. 10, it is possible to irradiate the tumor A located in the isocenter C0 with the higher dose than that located in the surrounding B.

In this case, since the burden of the head swing mechanism 301 is small, the irradiation accuracy is unlikely to be lowered due to the deflection of the head swing mechanism 301, and the affected area can be irradiated with the radiation with the high accuracy.

What is claimed is:

1. A radiation therapy system, comprising:
   a radiation source;
   a rotation mechanism that supports the radiation source and rotates the radiation source around an isocenter;
   a couch that places a therapy target site of a patient at the isocenter;
   a head swing mechanism that is disposed between the radiation source and the rotation mechanism and that swings an irradiation axis of a radiation emitted from the radiation source by swinging the radiation source; and
   a controller that controls the radiation source, the rotation mechanism, and the head swing mechanism, wherein
   the controller holds the head swing mechanism in a state where the irradiation axis of the radiation of the radiation source is shifted from the isocenter in a predetermined direction by a predetermined amount, and rotates the radiation source by the rotation mechanism while emitting the radiation from the radiation source while maintaining the state of the head swing mechanism,
   a direction in which the controller shifts the irradiation axis from the isocenter includes a component in a rotation axis direction of the rotation mechanism, and
   the controller shifts the irradiation axis from the isocenter in a positive direction in the rotation axis direction, rotates the radiation source by the rotation mechanism in this state, and then shifts the irradiation axis from the isocenter in a negative direction in the rotation axis direction, and rotates the radiation source by the rotation mechanism in this state.

2. The radiation therapy system according to claim 1, wherein
   the controller sets a shift amount of the irradiation axis of the radiation from the isocenter by the head swing mechanism such that the isocenter is included in a range of a spread angle of the radiation emitted from the radiation source.

3. The radiation therapy system according to claim 2, wherein
   an irradiation dose of the radiation in a region including the isocenter is larger than an irradiation dose outside the region.

4. The radiation therapy system according to claim 1, wherein
   a direction in which the controller shifts the irradiation axis from the isocenter includes a component in a radial direction of rotation of the rotation mechanism.

5. The radiation therapy system according to claim 1, wherein
   a multi-leaf collimator is disposed between subject sides of the radiation source, and shields a part of the radiation emitted from the radiation source while rotating with the radiation source by the rotation mechanism.

6. A method of operating a radiation therapy apparatus, comprising:
   shifting an irradiation axis of radiation of a radiation source from an isocenter by a predetermined amount in a predetermined direction by a head swing mechanism of the radiation source; and
   rotating the radiation source by a rotation mechanism while emitting the radiation from the radiation source while maintaining the above state, wherein
   a direction in which the irradiation axis is shifted from the isocenter includes a component in a rotation axis direction of the rotation mechanism, and
   the irradiation axis is shifted from the isocenter in a positive direction in the rotation axis direction, the radiation source is rotated by the rotation mechanism in this state, and then the irradiation axis is shifted from the isocenter in a negative direction in the rotation axis direction, and the radiation source is rotated by the rotation mechanism in this state.

* * * * *